US008975299B2

(12) United States Patent
Bar Yosef et al.

(10) Patent No.: US 8,975,299 B2
(45) Date of Patent: Mar. 10, 2015

(54) LIPID MIXTURE FOR INFANT NUTRITION

(75) Inventors: Fabiana Bar Yosef, Haifa (IL); Dori Pollod, Hod Hasharon (IL); Ariel Katz, Zichron Ya'akov (IL)

(73) Assignee: Enzymotec Ltd., Migdal Haemek (IL)

( * ) Notice: Subject to any disclaimer, the term of this patent is extended or adjusted under 35 U.S.C. 154(b) by 598 days.

(21) Appl. No.: 12/740,543

(22) PCT Filed: Nov. 2, 2008

(86) PCT No.: PCT/IL2008/001437
§ 371 (c)(1), (2), (4) Date: Jul. 21, 2010

(87) PCT Pub. No.: WO2009/057121
PCT Pub. Date: May 7, 2009

(65) Prior Publication Data

US 2010/0298273 A1 Nov. 25, 2010

Related U.S. Application Data

(60) Provisional application No. 60/996,109, filed on Nov. 1, 2007.

(51) Int. Cl.

| | |
|---|---|
| ***A61K 31/20*** | (2006.01) |
| ***A61K 31/685*** | (2006.01) |
| ***A61K 31/00*** | (2006.01) |
| ***A61K 31/683*** | (2006.01) |
| ***A23L 1/33*** | (2006.01) |
| ***A23L 1/29*** | (2006.01) |
| ***A23L 1/30*** | (2006.01) |

(52) U.S. Cl.
CPC ............... *A23L 1/296* (2013.01); *A23L 1/3008* (2013.01); *Y10S 426/801* (2013.01)
USPC ............... 514/558; 514/560; 514/25; 514/48; 514/51; 426/648; 426/33; 426/801; 426/601

(58) Field of Classification Search
USPC ......................................................... 514/114
See application file for complete search history.

(56) References Cited

U.S. PATENT DOCUMENTS

| | | | | |
|---|---|---|---|---|
| 2004/0143013 | A1 * | 7/2004 | Schade et al. | 514/560 |
| 2004/0265462 | A1 | 12/2004 | Carlson | |
| 2005/0129738 | A1 * | 6/2005 | Rutenberg | 424/439 |
| 2005/0130937 | A1 * | 6/2005 | Ben Dror et al. | 514/78 |

FOREIGN PATENT DOCUMENTS

| | | |
|---|---|---|
| CN | 1842277 | 10/2006 |
| DE | 19644518 | 4/1998 |
| WO | 2005051091 | 6/2005 |
| WO | 2005054415 | 6/2005 |
| WO | WO 2005051091 A1 * | 6/2005 |
| WO | 2007073192 | 6/2007 |
| WO | WO 2009047754 A2 * | 4/2009 |

OTHER PUBLICATIONS

Lucas et al, Arch. Dis. in Childhood, 1997, 77, F178-F184.*

European Commision Report May 18, 2003, "Report of the Scientific Committee on Food on the Revision of Essential Requirements of Infant Formulae and Follow-on Formulae", http://ec.europa.eu/food/fs/sc/scf/out199_en.pdf.*

Thompkin and Suman Kharb D K: "Aspects of Infant Food Formulation" Comprehensive Reviews in Food Science and Food Safety, vol. 6, No. 4, 2007, pp. 79-102.

Sala Vila A et al: "High-performance liquid chromatography with evaporative light-scattering detection for the determination of phospholipid classes in human milk, infant formulas and phospholipid sources of long-chain polyunsaturated fatty acids" Journal of Chromatography, Elsevier Science Publishers B.V. Amersterdam, NL, vol. 1008, No. 1, Aug. 1, 2003 (Aug. 1, 2003), pp. 73-80.

Sala Vila A et al: "The source of long-chain PUFA in formula supplements does not affect the fatty acid composition of plasma lipids in full-term infants" Journal of Nutrition, Wistar Institute of Anatomy and Biology, Philadelphia, PA, US, vol. 134, Jan. 1, 2004 (Jan. 1, 2004), pp. 868-873.

Voigt R G et al: "Relationship between u3 long-chain polyunsaturated fatty acid status during early infancy and neurodevelopmental status at 1 year of age" Journal of Human Nutrition and Dietetics, vol. 15, No. 2, 2002, pp. 111-120.

Yeh Yu-Yan et al: "Dietary supplementation with arachidonic and docosahexaenoic acids has no effect on pulmonary surfactant in artificially reared infant rats" Lipids, Champaign, IL, US, vol. 34, No. 5, May 1, 1999 (May 1, 1999), pp. 483-488.

* cited by examiner

*Primary Examiner* — Brian-Yong Kwon
*Assistant Examiner* — Kauser M Akhoon
(74) *Attorney, Agent, or Firm* — Maryellen Feehery Hank; Reed Smith LLP

(57) ABSTRACT

The subject invention thus provides a composition comprising at least one triglyceride, at least one phospholipid and at least one poly-unsaturated fatty acids (LC-PUFA); wherein at least about 1% of the LC-PUFA in the composition is conjugated to said at least one phospholipid and uses thereof.

30 Claims, No Drawings

LIPID MIXTURE FOR INFANT NUTRITION

RELATED APPLICATIONS

This application is the United States National Stage of International Application No. PCT/IL2008/001437, filed Nov. 2, 2008, which was published as International Publication No. WO 2009/057121, and which claims benefit of U.S. Patent Application No. 60/996,109 filed Nov. 7, 2007. Both applications are incorporated by reference in their entirety herewith.

FIELD OF THE INVENTION

This invention relates to the field of infant nutrition.

BACKGROUND OF THE INVENTION

The quantity and quality of nutrient supply during infancy has immediate consequences on growth, body composition, health, and well-being and has important long-term consequences on organ development and function, disease risks, as well as cognitive ability in later life.

In human breast milk (HBM), about 50% of the dietary calories are supplied as milk fat. Human Milk Fat (HMF) is composed of about 30-40 g/L lipids. Of those, approximately 98% are triglycerides, 0.3-1% phospholipids, and 0.4% cholesterol [WO05/051091, WO 06/114791].

(Dietary) lipids, such as those found in HBM, are indispensable for e.g. normal growth and development as major building blocks of cell membranes and tissues, and are e.g. important in signal transduction processes and in a variety of biochemical and biosynthetic pathways. Many lipids, and especially triglycerides, are part of human nutrition on a daily basis.

Triglyceride fats, or triglycerides, are the main energy source of newborn infants (Hamosh et al., *Pediatrics* 1985, 75 (suppl):146-150). In addition to providing 40% to 50% of the total calories in human milk or formula, triglycerides are essential to normal development since they provide fatty acids necessary for brain development, are an integral part of cell membranes, and are a vehicle for fat soluble vitamin and hormones in milk. Furthermore, these energy rich triglycerides can be stored in the body in nearly unlimited amounts in contrast to the limited storage capacity for carbohydrates and proteins.

The triglyceride composition of HMF is unique in its fatty acid composition and distribution. HMF is characterized in a total palmitic acid (C16:0) content of about 17-25%, of which about 70% are positioned at the sn-2 position of triglycerides [WO 05/051091]. Additionally, sn-1 and sn-3 positions are rich in unsaturated fatty acids, especially monounsaturated fatty acids, such as oleic acid (C18:1), which is of great importance to the infant's nutrition and development.

The sn-1 and sn-3 positions of vegetable fats are rich in saturated fatty acids and are thus not suitable for infant nutrition. Hence, advanced infant formulas include structured fats produced to mimic the unique structure and characteristics of HMF.

Phospholipids are an essential nutritional component of HBM. Although phospholipid composition remains constant and is not influenced by a mother's diet, the level of phospholipids in HBM changes with the age of the infant.

Phospholipids are composed of five major moieties: sphingomyelin (SM), phosphatidylcholine (PC), phosphatidylethanolamine (PE), phosphatidylserine (PS), and phosphatidylinositol (PI). [Thompkinson D K et al. *Comprehensive Reviews In Food Science And Food Safety* 6:79-102 (2007)].

Some phospholipids, and especially those extracted from soybean, are used as dietary supplements and a variety of health benefits are associated with their intake. These benefits include the improvement of cognitive functions, improvement of memory and concentration, maintenance of cellular membrane composition, and contribution to general well-being. Phospholipids and lecithins are a source of choline and they enhance the bio-availability of other nutrients and therapeutics.

Poly-unsaturated fatty acid (PUFA) levels in HBM vary widely depending on the type of fat consumed by a mother. Still, compared to cow milk fat, a fairly broad spectrum of fatty acids and a high content of unsaturated fatty acids, particularly linoleic acid, are present in HBM. In formulae based on cow milk on the other hand, blends of vegetable oil are added to provide an adequate amount of PUFAs, including linoleic acid and others.

Also glycerophospholipids, sphingomyelin, cholesterol and their derivatives, even though they are found in relatively small amounts in HBM, play an important role in nutrition of developing infants, and play essential roles in all physiological systems and cycles of the human body.

Infants who cannot be breast-fed or who should not receive HBM, or for whom HBM is not available, require breast milk substitutes. The most appropriate alternatives to human milk are infant formulae. Such industrially prepared formulae are based on bovine milk or are derived from a vegetarian source such as soybeans, and try to simulate the composition and biological properties of HBM. These known substitutes attempt to mimic the triglyceride content of HBM.

It is an object of the present invention to provide an improved substitute human milk composition comprising the imperative building blocks found in HMF comprising triglycerides, phospholipids and fatty acids, having benefits associated with mental and physical development of an infant together with benefits associated with intestinal development and function of an infant.

SUMMARY OF THE INVENTION

The subject invention thus provides a composition comprising at least one triglyceride, at least one phospholipid and at least one long chain poly-unsaturated fatty acid (LC-PUFA); said at least on triglyceride being a compound of formula I:

(I)

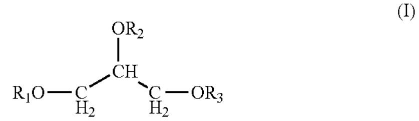

wherein $R_1$, $R_2$ and $R_3$ may be identical or different and are each independently selected from H or an acyl group, wherein the acyl group is selected from saturated fatty acid, mono-unsaturated fatty acid and long chain poly-unsaturated fatty acid (LC-PUFA) residues;

said at least one phospholipid being a compound of formula II:

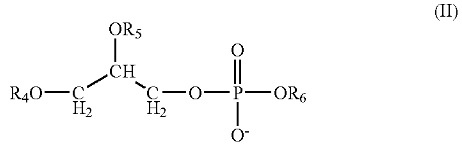

in which $R_4$ and $R_5$ are each a substituent having independently the meanings of $R_1$, $R_2$, $R_3$; and in which $R_6$ is selected from choline, inositol, ethanolamine and serine; and wherein at least about 1% of the LC-PUFA in the composition is conjugated to said at least one phospholipid.

The subject invention further provides uses of the compositions of the invention.

DETAILED DESCRIPTION OF THE INVENTION

In a first aspect of the invention, there is provided a composition comprising at least one triglyceride, at least one phospholipid and at least one long chain poly-unsaturated fatty acid (LC-PUFA); said at least on triglyceride being a compound of the following formula I:

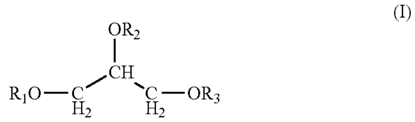

wherein $R_1$, $R_2$ and $R_3$ may be identical or different and are each independently selected from H or an acyl group, wherein the acyl group is selected from saturated fatty acid, mono-unsaturated fatty acid and long chain poly-unsaturated fatty acid (LC-PUFA) residues;

said at least one phospholipid being a compound of the following formula II:

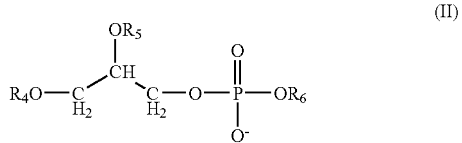

in which $R_4$ and $R_5$ are each a substituent having independently the meanings of $R_1$, $R_2$, $R_3$; and in which $R_9$ is selected from choline, inositol, ethanolamine and serine; and wherein at least about 1% of the LC-PUFA in the composition is conjugated to said at least one phospholipid.

A composition (blend) of the invention typically comprises a mixture of said triglycerides of formula I, said phospholipids of formula II and LC-PUFAs (in free form and in conjugated form). A mixture of the invention typically comprises two or more triglycerides of formula I, two or more phospholipids of formula II and LC-PUFAs, wherein the mixture typically comprises (i) free LC-PUFAs, (ii) LC-PUFAs conjugated to the triglycerides ($R_1$ and/or $R_2$ and/or $R_3$) and (iii) LC-PUFAs conjugated to the phospholipids ($R_4$ and/or $R_5$).

In one embodiment, said LC-PUFA is one or both of an omega-3 or an omega 6 fatty acid. In a specific embodiment said LC-PUFA comprises docosahexaenoic acid (DHA) and/or arachidonic acid (AA).

In one embodiment, the weight content of AA is larger than that of DHA. In a further embodiment, the weight content ratio between AA and DHA is at least about 1.1. In a further embodiment, the weight content ratio between AA and DHA is at least about 1.3. In yet a further embodiment, the weight content ratio between AA and DHA is at least about 1.5. In a further embodiment, the weight content ratio between AA and DHA is at least about 2. In yet another embodiment, the weight content ratio between AA and DHA is at least about 3. In another embodiment, the weight content ratio between AA and DHA is at least about 10.

In a further embodiment, $R_5$ is an LC-PUFA residue. In another embodiment, said LC-PUFA residue is an omega-3 or an omega-6 fatty acid residue. In a further specific embodiment, said LC-PUFA is DHA or AA.

In yet a further embodiment, $R_4$ is an LC-PUFA residue. In another embodiment, said LC-PUFA residue is an omega-3 or an omega-6 fatty acid residue. In a further specific embodiment, said LC-PUFA is DHA or AA.

In a specific embodiment, at least about 2% (w/w) of the LC-PUFA content of the formulation is conjugated to at least one phospholipid. In yet a further embodiment at least about 5% (w/w) of the LC-PUFA content of the formulation is conjugated to at least one phospholipid. In yet a further embodiment at least about 10% (w/w) of the LC-PUFA content of the formulation is conjugated to at least one phospholipid. In another embodiment at least about 20% (w/w) of the LC-PUFA content of the foimulation is conjugated to at least one phospholipid. In yet another embodiment at least about 50% (w/w) of the LC-PUFA content of the formulation is conjugated to at least one phospholipid.

In one embodiment, at least 1% of the conjugated LC-PUFA is conjugated at position sn-2 of said at least one phospholipids. In a further embodiment, at least about 2% of the conjugated LC-PUFA is conjugated at position sn-2 of said at least one phospholipid. In another embodiment, at least about 33% of the conjugated LC-PUFA is conjugated at position sn-2 of said at least one phospholipid. In a further embodiment, at least about 40% of the conjugated LC-PUFA is conjugated at position sn-2 of said at least one phospholipid. In yet another embodiment, at least about 45% of the conjugated LC-PUFA is conjugated at position sn-2 of said at least one phospholipid. In another embodiment, at least about 50% of the conjugated LC-PUFA is conjugated at position sn-2 of said at least one phospholipid. In yet a further embodiment, at least about 60% of the conjugated LC-PUFA is conjugated at position sn-2 of said at least one phospholipid. In another embodiment, at least about 70% of the conjugated LC-PUFA is conjugated at position sn-2 of said at least one phospholipid.

In another embodiment the total amount of phospholipids in the composition is at least about 0.1%. In another embodiment, the total amount of phospholipids in the composition is at least about 0.5%. In a further embodiment, the total amount of phospholipids in the composition is at least about 1%. In another embodiment, the total amount of phospholipids in the composition is at least about 2%. In another embodiment, the total amount of phospholipids in the composition is at least about 5%. In a further embodiment, the total amount of phospholipids in the composition is at least about 7%. In a further embodiment, the total amount of phospholipids in the composition is at least about 10%. In a further embodiment, the total amount of phospholipids in the composition is at least about 15%. In a further embodiment, the total amount of phospholipids in the composition is at least about 20%. In a further embodiment, the total amount of phospholipids in the composition is at least about 35%. In a further embodiment, the total amount of phospholipids in the composition is at least about 50%.

In a further embodiment, said triglyceride and/or said phospholipid are derived from at least one raw lecithin material selected from the group consisting of vegetable, marine and aquaculture organism.

In one aspect of the present invention, there is provided a pharmaceutical composition comprising a composition of the present invention.

Suitable routes of administration for the compositions of the subject invention are oral, buccal, sublingual, via feeding tube, topical, transdermal, or parenteral (including subcutaneous, intramuscular, intravenous and intradermal) administration. In a specific embodiment, the compounds can be administered orally.

The exact dose and regimen of administration of the composition will necessarily be dependent upon the therapeutic or nutritional effect to be achieved and may vary with the particular formula, the route of administration, and the age and condition of the individual subject to whom the composition is to be administered.

The present invention thus also provides pharmaceutical compositions of the invention in admixture with pharmaceutically acceptable auxiliaries, and optionally other therapeutic agents. The auxiliaries must be "acceptable" in the sense of being compatible with the other ingredients of the composition and not deleterious to the recipients thereof.

In one embodiment, the pharmaceutical composition further comprises at least one pharmaceutically active agent.

The compositions of the invention may be prepared by any method well known in the art of pharmacy. Such methods include the step of bringing in association the ingredients with any auxiliary agent. The auxiliary agent(s), also named accessory ingredient(s), include those conventional in the art, such as carriers, fillers, binders, diluents, disintegrants, lubricants, colorants, flavouring agents, anti-oxidants, and wetting agents.

Pharmaceutical compositions suitable for oral administration may be presented as discrete dosage units such as pills, tablets, dragées or capsules, or as a powder or granules, or as a solution or suspension.

For parenteral administration, suitable compositions include aqueous and non-aqueous sterile injection. The compositions may be presented in unit-dose or multi-dose containers, for example sealed vials and ampoules, and may be stored in a freeze-dried (lyophilised) condition requiring only the addition of sterile liquid carrier, for example water, prior to use. For transdermal administration, e.g. gels, patches or sprays can be contemplated.

The invention further provides a commercial package for preparing a formula comprising: (a) a composition according to the invention which upon administration to a subject for example, improves, maintains or treats conditions associated with mental and physical development of an infant, (b) optionally at least one of physiologically acceptable protein, carbohydrate, vitamin, mineral, amino acid, nucleotide and active or non-active additive; (c) optionally at least one physiologically acceptable carrier or diluent for carrying the constituent/s defined in (a) and (b); (d) means and receptacles for admixing the constituents defined in (a), (b) and/or (c); and (e) instructions for use such as, but not limited to terms of storage, instructions for preparation of the formula for administration, required dilutions, dosages, frequency of administration and the like.

A commercial package in accordance with the invention may also contain a composition of the invention in a ready-to-use form, together with instructions for use. Dosages are usually determined according to age, weight, sex and condition of the subject, in accordance with good medical practice known to the attending physician and other medical personnel.

In order to obtain a desired formula of the invention, a composition of the invention may be mixed with other components such as, but not limited to a protein source, a carbohydrate source, minerals, vitamins, nucleotides, amino acids and optionally at least one of a carrier, diluent, additive or excipient, all of which are suitable for mammal consumption and/or administration and are pharmaceutically acceptable.

In one aspect of the present invention there is provided a nutritional composition comprising a composition of the invention.

A nutritional composition as used herein can be any nutritional composition including, but not limited to, human milk fat substitute, infant formula, dairy product, ice-cream, biscuit, soy product, bakery, pastry and bread, sauce, soup, prepared food, frozen food, condiment, confectionary, oils and fat, margarine, spread, filling, cereal, instant product, infant food, toddler food, bar, snack, candy and chocolate product.

In another aspect of the invention, there is provided a nutraceutical composition comprising a composition of the invention.

A nutraceutical composition as used herein can be any nutraceutical, which can be any substance that may be considered a food or part of a food and provides medical or health benefits, including the prevention and treatment of disease. Such nutraceutical compositions include, but are not limited to, a food additive, a food supplement, a dietary supplement, genetically engineered foods such as for example vegetables, herbal products, and processed foods such as cereals, soups and beverages and stimulant functional food and pharmafood.

In yet a further aspect of the invention there is provided a functional food comprising a composition according of the invention.

A functional food as used herein can be any functional food, including, but not limited to, dairy product, ice-cream, biscuit, soy product, bakery, pastry and bread, sauce, soup, prepared food, frozen food, condiment, confectionary, oils and fat, margarine, spread, filling, cereal, instant product, drinks and shake, infant food, toddler food, bar, snack, candy and chocolate product.

In a further aspect of the invention there is provided an infant formula comprising a composition of the invention.

An infant as used herein is meant to encompass a human infant or any non-human mammal infant. An infant as used herein is meant to encompass any infant, such as, but not limited to, a newborn, a preterm and term infant, small premature infants, infants with very low birth weight (VLBW) or extreme low birth weight (ELBW) particularly those with general immaturity, for example of the gastrointestinal track or any other health risks known to a person skilled in the art.

In another aspect of the invention there is provided a method for improving, promoting or maintaining the development of cognitive functions in an infant comprising administering to said infant a composition of the invention.

The phrase "improving, promoting or maintaining" as used herein is meant to encompass enhancing, advancing, supporting, progressing, retaining, keeping, preserving or sustaining any desired developmental function in a mammalian infant. Such developmental functions include, but are not limited to, development of cognitive functions in an infant, development of brain and retina in an infant, development of visual acuities in an infant, reduction of lipid peroxidation in an infant, growth quality of an infant, central nervous system (CNS) development in an infant and so forth.

The term "development of cognitive functions in an infant" as used herein is meant to encompass the development of a range of functions and abilities such as, but not limited to, intelligence, creativity (generate and open to new ideas, perceive new relationships), memory (encoding, storage, retrieval), executive functions (dealing with novelty, planning and implementation, monitoring performance, vigilance, inhibition of task irrelevant info), cognitive resources (speed of information processing, working memory capacity, attentional capacity), attention, learning, perception, action, planning, problem solving and mental imagery.

A well known method of assessing cognitive development in an infant is an assessment of the infant's mental development index (MDI) in accordance with the Bayley neurodevelopmental scales (*Bayley, N. The Bayley Scales of Infant Development II. New York: New York Psychological Corp.*, 1993).

In a further aspect of the invention, there is, provided a method for improving, promoting or maintaining the development of brain and retina in an infant comprising administering to said infant a composition of the invention.

The term "development of brain and retina in an infant" as used herein is meant to encompass processes such as, but not limited to, those resulting in progression of the brain and retina over time, from its formation to the mature structure. The result of brain development is responsible for the coordination and control of bodily activities and the interpretation of information from the senses (such as for example sight, hearing, smell, etc.).

In another aspect of the invention, there is provided a method for improving, promoting or maintaining the development of visual acuities in an infant comprising administering to said infant a composition of the invention.

The term "development of visual acuities in an infant" as used herein is meant to encompass the eye's ability to resolve fine details or small distances, as measured by any means suitable in the art, including electro-retinography. "Enhanced visual acuity" refers to any improvement in the eye's ability to resolve fine details or small distances, as measured by any means suitable in the art.

By another one of its aspects the present invention provides a method for reducing lipid peroxidation in an infant comprising administering to said infant a composition of the invention.

The term "reducing lipid peroxidation in an infant" as used herein is meant to encompass the amelioration, prevention, slowing down of the oxidative deterioration of lipids containing any number of carbon-carbon double bonds and preventing inflammation.

By a further aspect of the invention, there is provided a method for improving, promoting or maintaining the growth quality of an infant by administering to said infant a composition of the invention.

The term "growth quality of an infant" as used herein is meant to encompass weight gain, changes in length and head circumference, and other additional physiological development as given in growth references data and physical examination procedures known to a person skilled in the art.

In another aspect of the invention, there is provided a method for improving, promoting or maintaining the CNS development in an infant comprising administering to said infant a composition of the invention.

The term "CNS development in an infant" as used herein is meant to encompass any processes such as, but not limited to, those resulting in the progression of the central nervous system over time, from its formation to the mature structure and function.

In yet a further aspect of the invention, there is provided a method for enhancing intestinal absorption of omega-3 and/or omega-6 fatty acids in healthy, non-healthy and preterm infants comprising administering to said infant the composition of the invention The term "enhancing intestinal absorption of omega-3 and/or omega-6 fatty acids" as used herein is meant to encompass improving and increasing processes such as, but not limited to, those by which nutrients omega-3 and/or omega-6 fatty acids are absorbed from the contents of the intestine.

In another aspect of the invention there is provided a method for improving, promoting or maintaining intestinal maturity in infants comprising administering to said infant the composition of the invention.

The term "improving, promoting or maintaining intestinal maturity in infants" as used herein is meant to encompass for example promoting of normal growth and maturation of the gastro-intestinal tract, restoring or maintaining gastrointestinal function, promoting villous growth, promoting proliferation of the small and large intestine in a healthy mammal, e.g., to enable increased absorption of nutrients.

The invention further encompasses a use of a composition of the invention, for the preparation of a pharmaceutical or nutraceutical composition for treatment of infants.

In one embodiment, a composition of the invention is prepared from a natural, synthetic or semi-synthetic source. In a further specific embodiment, said natural source is any one of plant, animal or microorganism source. In yet a further embodiment, the production of said lipid composition involves an enzymatic catalysis.

In another embodiment, a composition of the invention may be synthesized by polar extraction from a marine, a plant, animal or micro-organisms source. Synthetic routs appropriate for synthesizing a composition of the invention are described in "*Lecithins: Sources Manufacture and uses*" Bernard F. Szuhaj Ed. (1989) which is herein incorporated by reference.

In an embodiment of the invention, the pharmaceutical or nutraceutical compositions are in a dosage delivery form.

In one embodiment, a composition of the subject invention further comprises at least one triglyceride of formula I, having at least 30% (w/w) of total palmitic acid conjugated at the sn-2 position.

In another embodiment, a composition of the subject invention further comprises (is mixed with) at least one triglyceride of formula I having the following conjugated fatty acid profile:

0-10% C8:0 fatty acids out of the total fatty acids;
0-10% C10:0 fatty acids out of the total fatty acids;
0-22% C12:0 fatty acids out of the total fatty acids;
0-15% C14:0 fatty acids out of the total fatty acids;
15-55% C16:0 fatty acids out of the total fatty acids of which at least 30% is conjugated at the sn-2 position of triglyceride;
1-7% C18:0 fatty acids out of the total fatty acids;
20-75% C18:1 fatty acids out of the total fatty acids;
2-40% C18:2 fatty acids out of the total fatty acids;
0-8% C18:3 fatty acids out of the total fatty acids; and other fatty acids present in levels of less than 8% of the total fatty acids.

As used herein, the term "acyl group" relates to an organic radical denoted —C(═O)R, wherein R is selected from saturated, mono-unsaturated and polyunsaturated fatty acid residue.

As used herein, the term "fatty acid" is meant to encompass a carboxylic acid with a unbranched aliphatic tail (chain) typically having between 4 and 28 carbon atoms, which is either saturated or unsaturated having one unsaturated bond (mono-unsaturated fatty acids) or two or more unsaturated bonds (poly-unsaturated fatty acids). It should be noted that when at least one unsaturated bond of an unsaturated fatty acid is at least one double bond, said at least one double bond may be either in the cis configuration or in the trans configuration.

Non-limiting examples of saturated fatty acids which may be used in this invention include: Butyric acid (Butanoic acid, C4:0), Caproic acid (Hexanoic acid, C6:0), Caprylie acid (Octanoic acid, C8:0), Capric acid (Decanoic acid, C10:0), Lauric acid (Dodecanoic acid, C12:0), Myristic acid (Tetradecanoic acid, C14:0), Palmitic acid (Hexadecanoic acid, C16:0), Stearic acid (Octadecanoic acid, C18:0), Arachidicaicd (Eicosanoic acid, C20:0), Behenic acid (Docosanoic acid C22:0).

Non-limiting examples of mono-unsaturated fatty acids which may be used in this invention include: Myristoleic acid (ω-5, C14:1), Palmitoleic acid (ω-7, C16:1), Oleic acid (ω-9, C18:1) and Erucic acid (ω-9, C22:1).

The term "long-chain polyunsaturated fatty acid (LC-PUFA)" as used herein is meant to encompass fatty acids with unbranched aliphatic chain having at least 18 carbon atoms and at least two unsaturated bonds.

Non-limiting examples of LC-PUFA are Alpha-linolenic acid (ALA, ω-3, C18:3), Eicosapentaenoic acid (EPA, ω-3, C20:5), Docosahexaenoic acid (DHA, ω-3, C22:6), Docosapentaenoic acid (DPA, ω-3, 22:5), Linoleic acid (LA, ω-6, C18:2), Arachidonic acid (AA, ω-6, C20:4).

The term "omega-3 fatty acid" as used herein is meant to encompass a carboxylic acid with a long unbranched aliphatic chain which is polyunsaturated, wherein the first carbon-carbon double bond is located at the ω-3 position (i.e. on the third carbon from the end of the aliphatic chain). Non limiting examples of omega-3 fatty acids which may be used in the composition of the invention include: Alpha-linolenic acid (ALA, ω-3, C18:3), Eicosapentaenoic acid (EPA, ω-3, C20:5), Docosahexaenoic acid (DHA, ω-3, C22:6) and Docosapentaenoic acid (DPA, ω-3, 22:5).

The term "omega-6 fatty acid" as used herein is meant to encompass a carboxylic acid with a long unbranched aliphatic chain which is polyunsaturated, wherein the first carbon-carbon double bond is located at the ω-6 position (i.e. on the sixth carbon from the end of the aliphatic chain). Non limiting examples of omega-6 fatty acids which may be used in the composition of the invention include: Linoleic acid (LA, ω-6, C18:2) and Arachidonic acid (AA, ω-6, C20:4).

The invention is further described in the following examples, which are not in any way intended to limit the scope of the inventions as claimed.

EXAMPLES

Example 1

Preparation of Lipid Fractions Used for the Preparation of Compositions (Blends) of the Invention Lipid Fraction 1: Extraction of Biomass Enriched with Archidonic Acid Mortierella Alpina, strain ATCC32222 was grown in 1 liter media in a 2 liter shake flask. Growth media was based on glucose (30 g/l) as carbon source and yeast extract (15 g/l) as Nitrogen source. In addition, the following components were added: Potassium dihydrogen phosphate $KH_2PO_4$ (7 g/l), Disodium hydrogen phosphate $Na_2HPO_4$ (2 g/l), Magnesium sulfate $MgSO_4.7H_2O$ (1.5 g/l), $CaCl_2.2H_2O$ (0.1 g/l), $FeCl_3.6H_2O$ (8 mg/l), $ZnSO_4.7H_2O$ (1 mg), $CuSO_4.5H_2O$ (0.1 mg/l), $Co(NO_3)_2.6H_2O$ (0.1 mg/l), $MnSO_4.5H_2O$ (0.1 mg/l). After 8 fermentation days at 28° C., the biomass was filtered, washed with DI water and dried in a vacuum oven at 25° C. to obtain 18 gr of dried biomass.

Lipid Fraction 2: Enrichment of Lipid Fraction 1

The dried biomass from lipid fraction 1 was subjected to an extraction procedure by mixing with 100 ml mixture of hexane and ethanol (80:20 v/v) for 2 hours at 40° C. in a shaker incubator at 200 RPM. Biomass was filtered and washed. The filtrate was evaporated under reduced pressure to obtain 5.1 gr of lipid fraction.

Lipid Fraction 3: Purification of Phospholipids Enriched with ARA

Oil essentially as produced in lipid fraction 2, was used as starting material to obtain a pure phospholipid fraction. 10 gr of the oil were dissolved in 30 ml of absolute ethanol and loaded on a glass column packed with 200 gr of silica (Merck 60). About 1 liter of absolute ethanol was passed through the column and the outlet was analyzed continuously by TLC until a pure phospholipids fraction started to elute. Further washing of the column was done with about 3 liters of ethanol 96% (4% water) by increasing temperature to 60° C. in order to remove more of the phospholipids fraction. This fraction was collected separately, evaporated under reduced pressure to obtain about 0.3 gr of pure phospholipids.

Lipid Fraction 4: Extraction of Lipid Fraction from *Schizochytrium* sp Biomass 50 gr of biomass of the micro alga *Schizochytrium* sp was subjected to an extraction procedure by mixing with 250 ml of ethanol 96% (4% water content) for 2 hours at 40° C. in a shaker incubator at 200 RPM. Biomass was filtered and washed. The filtrate was evaporated under reduced pressure to obtain 8.7 gr of oil.

Lipid Fraction 5: Selective Extraction of Lipid Fraction with High Triglycerides Content 20 gr Biomass of the micro alga *Schizochytrium* sp was subjected to an extraction procedure by mixing with 100 ml of acetone for 2 hours at ambient temperature with a magnetic stirrer. Biomass was filtered and washed. The filtrate was evaporated under reduced pressure to obtain 7.7 gr of oil.

Lipid Fraction 6: Selective Extraction of Lipid Fraction with High Phospholipids Content The biomass obtained after production of lipid fraction 5 by acetone extraction was subjected to an additional extraction using 100 ml of hexane:ethanol (80:20 v/v) solvent mixture at temperature of 40° C. for 2 hours in a shaker incubator at 200 RPM. After filtration and evaporation of the filtrate, 0.6 gr of paste-like material was obtained.

Lipid Fraction 7: Purification of Phospholipids Enriched with DHA 10 gr of paste-like material essentially as produced in lipid fraction 6, was used as a starting material for phospholipids purification process as described in order to produce lipid fraction 3. From 10 gr of feed 0.6 gr of pure phospholipids fraction was obtained.

Lipid Fraction 8: Industrial Production of Lipid Fraction Enriched with Phospholipids 1,000 Kg of fish meal from Herring source was extracted using 4,000 liters mixture of ethanol:water (80:20 v/v) for 2 hours at 40° C. in a 5,000 liters reactor equipped with an anchor type agitator. Biomass was filtered in a 1.5 m diameter basket centrifuge and washed. The filtrate was evaporated under vacuum using hot water in the jacket, in a 3,000 batch evaporator equipped with a propeller type agitator. The paste like material obtained was re-dissolved in hexane, filtered again through a bag filter and evaporated in the same evaporator under the same conditions to obtain 46 Kg of a highly viscous lipid fraction.

Methods for Determination of the Content of the Lipid Fractions:

1. Determination and Quantification of Fatty Acid Composition:

Fatty acid methyl esters were prepared by basic methylation in the presence of sodium methoxide dissolved in methanol and extracted by hexane. Fatty acid composition was analyzed by injection of the methyl esters into Gas-Chromatograph instrument equipped with a capillary column and flame ionization detector.

The GC (HP) instrument programmed under the following conditions:

OVEN—Initial temp—110° C., Final temp—250° C., Run time—41.50 min

FRONT INLET—Initial temp—350° C., Pressure—13.83 psi, Split ratio—24.988:1, Split flow—39.8 ml/min, Total flow—43.4 ml/min, Gas type—nitrogen FRONT DETECTOR—Temp.—250° C., Hydrogen flow—40.0 ml/min, Air flow—400.0 ml/min The quantification of the methyl esters was performed against internal standard of C23:0.

2. Determination and Quantification of Phospholipid Content

Phospholipids content was measured either by $^{31}$P-NMR or by HPTLC.

$^{31}$P-NMR is a an accepted and widely used method for measuring phospholipid content (*Analytical Biochemistry Volume* 232, Issue 1, November 1995, Pages 1-6*; Journal of Lipid Research Volume* 27, 1986, 386).

HPTLC method consists of applying a sample containing phospholipids on Silica plate, develop the plate in solvent mixture (Chloroform:Acetone:Methanol:Acetic acid and water=11:6.4:5:2.4:1 (v/v)). After the development the plate is dried and stained with mixture of acidic $CuSO_4$. The quantification is performed by scanning the plate at 274 nm versus mixture of known phospholipid content.

3. Determination and Quantification of Triglyceride Content

The quantification of the triglycerides content was performed by injection of the sample into the GC instrument equipped with a capillary column and flame ionization detector. The GC is equipped with Agilent column model J&W DB-1HT and programmed under the following conditions:

OVEN—Initial temp—160 c, Final temp—350 c, Run time—29.50 min

FRONT INLET—Initial temp—350 c, Pressure—13.83 psi, Split ratio—24.988:1, Split flow—39.8 mL/min, Total flow—43.4 mL/min, Gas type—nitrogen FRONT DETECTOR—Temp.—350 c, Hydrogen flow—40.0 mL/min, Air flow—400.0 mL/min 4. Analysis of Phospholipids Fatty Acid Composition Fatty acid composition esterified to the phospholipids was analyzed by two-step process. The analyzed phospholipids were purified on thin-layer chromatography (TLC) plate (by the same solvent mixture of method 2), scrubbed from the silica with toluene and transformed to methyl esters following procedure number 1.

5. Positional Analysis of Fatty Acid

Analysis of the positional distribution of phospholipids fatty acid was carried out by a multistage procedure starting with a selective hydrolysis of the sn-2 fatty acid by phospholipase A2 (PLA2). The resulting 2-lyso-phosphlipid fraction was purified on a silica plate, transformed to methyl esters and analyzed by the GC as previously described procedure.

Table 1 details the composition of several lipid preparations, comprising triglycerides and phospholipids for use in the preparation of compositions of the subject invention.

TABLE 1

| | lipid fractions | | | | | | |
|---|---|---|---|---|---|---|---|
| | lipid fraction 2 | lipid fraction 3 | lipid fraction 4 | lipid fraction 5 | lipid fraction 6 | lipid fraction 7 | lipid fraction 8 |
| % Phospholipids | 5.2 | >95 | 1.8 | <5 | 12.0 | >95 | 45 |
| % Triglycerides | 83.0 | <5 | NM | 96.0 | NM | <5 | NM |
| Fatty acid (% w/w) of total fatty acids | | | | | | | |
| C14 | 1.1 | 0.4 | 6.6 | 6.0 | 2.8 | 1.3 | |
| C16 | 13.8 | 9.6 | 25.1 | 25.2 | 14.9 | 16.6 | |
| C18 | 9.1 | 2.4 | 0.6 | 0.6 | 0.3 | 0.3 | 1.3 |
| C18:1n9 | 12.8 | 8.9 | 1.0 | | | 0.2 | 3.9 |
| C18:2 n6 | 5.6 | 8.4 | 1.0 | | | 0.4 | 1.0 |
| C18:3 n3 | 3.9 | 6.1 | 0.4 | 0.4 | | | 0.2 |
| C20:3n6 | 4.1 | 2.1 | 2.5 | | | 0.4 | |
| C20:4n6 | 41.2 | 21.3 | 1.3 | 1.3 | 0.9 | 1.2 | 0.5 |
| C20:5n3 | | | 3.4 | 3.2 | 2.7 | 4.9 | 5.7 |
| C22:5n3 | | | 16.3 | 17.7 | 10.4 | 12.3 | |
| C22:6n3 | | | 36.4 | 38.7 | 22.7 | 26.4 | 16.3 |
| Fatty acid (% of fatty acid esterified to Phospholipids) | | | | | | | |
| C14 | 0.5 | 0.5 | 1.4 | | 1.8 | 1.8 | 2.2 |
| C16 | 13.7 | 13.7 | 21.7 | | 23.7 | 23.7 | 29.8 |
| C18 | 3.4 | 3.4 | 0.4 | | 0.4 | 0.4 | 2.2 |
| C18:1n9 | 12.7 | 12.7 | 1.2 | | 0.2 | 0.2 | 18.0 |
| C18:2 n6 | 12.1 | 12.1 | 3.1 | | 0.6 | 0.6 | |
| C18:3 n3 | 8.8 | 8.8 | | | | | |
| C20:3n6 | 3.1 | 3.1 | 0.8 | | 0.6 | 0.6 | |
| C20:4n6 | 30.4 | 30.4 | 2.1 | | 1.7 | 1.7 | |

TABLE 1-continued

| | lipid fractions | | | | | | |
|---|---|---|---|---|---|---|---|
| | lipid fraction 2 | lipid fraction 3 | lipid fraction 4 | lipid fraction 5 | lipid fraction 6 | lipid fraction 7 | lipid fraction 8 |
| C20:5n3 | | | 6.4 | | 7.0 | 7.0 | 12.0 |
| C22:5n3 | | | 19.7 | | 17.5 | 17.5 | |
| C22:6n3 | | | 32.2 | | 37.7 | 37.7 | 31.0 |
| LC-PUFA | | | | | | | |
| Total LC-PUFA % w/w | 54.8 | 38.0 | 61.2 | 61.3 | 36.7 | 45.5 | 23.8 |
| % LC-PUFA on PL from total LC-PUFA | 3.6 | >95 | 1.3 | | 14.9 | >95 | 56.9 |
| % LC-PUFA at sn-2 of PL from total LC-PUFA of PL | >50 | >50 | >50 | | >50 | >50 | 82.9 |

NM = not measured

% Total LC-PUFA represents sum of % w/w of C18:2, C18:3, C20:3, C20:4, C20:5 and C22:6 fatty acids.

% LC-PUFA on PL from total LC-PUFA is calculated by (LC-PUFA on PL as % w/w)/(Total LC-PUFA as % w/w) *100.

% LC-PUFA at the sn-2 of phospholipids from total LC-PUFA on phospholipids is calculated by (% LC-PUFA at sn-2 of total sn-2 positioned fatty acids)/(total LC-PUFA on phospholipids)*100.

% LC-PUFA at the sn-2 of phospholipids from total LC-PUFA on phospholipids>50 is not based on a measured value but on an estimated value.

Compositions (blends) of the invention comprising LC-PUFA enriched oils (Table 2) were prepared by mixing lipid fractions 2-8 (Table 1) with each other.

Blends of the invention can further optionally be mixed with a fat blend such as, but not limited to, an sn-2 palmitic acid enriched fat blend as described in PCT/IL2008/001311 (Table 5).

Optionally components from lipid fractions 4 and 6 are passed through a sequence of refining stages including, degumming, bleaching and deodorization before use in the blending procedure.

TABLE 2

| | LC-PUFA enriched compositions (blends) | | | | | | | | |
|---|---|---|---|---|---|---|---|---|---|
| | blend 1 | blend 2 | blend 3 | blend 4 | blend 5 | blend 6 | blend 7 | blend 8 | blend 9 |
| lipid fraction mixed (%) | | | | | | | | | |
| lipid fraction 2 | 50.0 | 43.5 | 54.5 | 73.2 | 28.6 | 90.1 | 50.0 | 47.6 | 40.0 |
| lipid fraction 3 | | 13.0 | 5.5 | 7.3 | 28.6 | | | 47.6 | |
| lipid fraction 4 | | | | | | | 50.0 | | |
| lipid fraction 5 | | | 36.4 | 7.3 | 28.6 | 9.0 | | 4.8 | |
| lipid fraction 6 | | 43.5 | 0.0 | 7.3 | | 0.9 | | | |
| lipid fraction 7 | 50.0 | | 3.6 | 4.9 | | | | | 60.0 |
| lipid fraction 8 | | | | | 14.3 | | | | |
| % Phospholipids | 52.6 | 20.5 | 11.9 | 16.9 | 36.5 | 4.8 | 3.5 | 50.1 | 62.1 |
| % Triglycerides | 41.5 | NC | 80.2 | NC | NC | NC | NC | 44.1 | 33.2 |
| Fatty acid (% w/w) of total fatty acids | | | | | | | | | |
| C14 | 1.2 | 1.7 | 2.8 | 1.5 | 2.1 | 1.5 | 3.9 | 1.0 | 1.2 |
| C16 | 15.2 | 13.7 | 17.8 | 14.5 | 13.9 | 14.8 | 19.4 | 12.3 | 15.4 |
| C18 | 4.7 | 4.4 | 5.3 | 6.9 | 3.7 | 8.3 | 4.9 | 5.5 | 3.8 |
| C18:1n9 | 6.5 | 6.7 | 7.5 | 10.0 | 6.8 | 11.6 | 6.9 | 10.3 | 5.2 |
| C18:2 n6 | 3.0 | 3.5 | 3.5 | 4.7 | 4.2 | 5.0 | 3.3 | 6.7 | 2.5 |
| C18:3 n3 | 1.9 | 2.5 | 2.6 | 3.3 | 3.0 | 3.5 | 2.1 | 4.8 | 1.5 |
| C20:3n6 | 2.3 | 2.1 | 2.4 | 3.2 | 1.8 | 3.7 | 3.3 | 3.0 | 1.9 |
| C20:4n6 | 21.2 | 21.1 | 24.1 | 31.9 | 18.3 | 37.2 | 21.2 | 29.8 | 17.2 |
| C20:5n3 | 2.4 | 1.2 | 1.3 | 0.7 | 1.7 | 0.3 | 1.7 | 0.2 | 2.9 |
| C22:5n3 | 6.1 | 4.5 | 6.9 | 2.7 | 5.1 | 1.7 | 8.2 | 0.8 | 7.4 |
| C22:6n3 | 13.2 | 9.9 | 15.1 | 5.8 | 13.4 | 3.7 | 18.2 | 1.8 | 15.8 |
| Fatty acid (% of fatty acid esterified to Phospholipids) | | | | | | | | | |
| C14 | 1.2 | 1.1 | 0.4 | 0.6 | 0.6 | 0.5 | 1.0 | 0.5 | 1.3 |
| C16 | 18.7 | 18.0 | 9.0 | 13.9 | 12.1 | 12.5 | 17.7 | 13.0 | 19.7 |
| C18 | 1.9 | 2.1 | 2.0 | 2.8 | 2.2 | 3.0 | 1.9 | 3.2 | 1.6 |
| C18:1n9 | 6.5 | 7.3 | 7.6 | 10.3 | 9.8 | 11.5 | 7.0 | 12.1 | 5.2 |
| C18:2 n6 | 6.3 | 7.1 | 7.3 | 9.8 | 6.9 | 10.9 | 7.6 | 11.5 | 5.2 |
| C18:3 n3 | 4.4 | 5.0 | 5.3 | 7.1 | 5.0 | 7.9 | 4.4 | 8.4 | 3.5 |
| C20:3n6 | 1.8 | 2.0 | 1.9 | 2.5 | 1.7 | 2.8 | 1.9 | 2.9 | 1.6 |
| C20:4n6 | 16.0 | 17.9 | 18.3 | 24.7 | 17.4 | 27.4 | 16.3 | 29.0 | 13.2 |
| C20:5n3 | 3.5 | 3.0 | 0.3 | 0.9 | 1.7 | 0.1 | 3.2 | 0.0 | 4.2 |

TABLE 2-continued

| LC-PUFA enriched compositions (blends) | | | | | | | | | |
|---|---|---|---|---|---|---|---|---|---|
| | blend 1 | blend 2 | blend 3 | blend 4 | blend 5 | blend 6 | blend 7 | blend 8 | blend 9 |
| C22:5n3 | 8.8 | 7.6 | 0.6 | 2.1 | 0.0 | 0.2 | 9.9 | 0.0 | 10.5 |
| C22:6n3 | 18.9 | 16.4 | 1.4 | 4.6 | 4.4 | 0.3 | 16.1 | 0.0 | 22.6 |
| LC-PUFA | | | | | | | | | |
| Total LC-PUFA % w/w | 50.2 | 44.7 | 55.9 | 52.3 | 47.4 | 55.2 | 58.0 | 47.1 | 49.2 |
| % LC-PUFA on PL from total LC-PUFA | 43.8 | 18.9 | 5.2 | 11.7 | 20.0 | 3.0 | 2.5 | 38.5 | 53.6 |
| % LC-PUFA at sn-2 of PL from total LC-PUFA of PL | >50 | >50 | >50 | >50 | >50 | >50 | >50 | >50 | >50 |
| AA:DHA | 1.6 | 2.1 | 1.6 | 5.5 | 1.4 | 10.1 | 1.2 | 16.2 | 1.1 |

NC = not calculated

% Total LC-PUFA represents sum of % w/w of C18:2, C18:3, C20:3, C20:4, C20:5 and C22:6 fatty acids.

% LC-PUFA on PL from total LC-PUFA is calculated by (LC-PUFA on PL as % w/w)/(Total LC-PUFA as % w/w) *100.

% LC-PUFA at the sn-2 of phospholipids from total LC-PUFA on phospholipids is calculated by (% LC-PUFA at sn-2 of total sn-2 positioned fatty acids)/(total LC-PUFA on phospholipids)*100.

Ratio ARA:DHA is calculated as C20:4 (% w/w of total fatty acids)/C22:6 (% w/w of total fatty acids).

Example 2

Infant Formula

Table 3 provides examples of known fat compositions of infant formula (first two columns of table 3), and an example of a fat composition of infant formula in accordance with the invention (third column of table 3).

Table 4 provides examples of known fat compositions of infant formula (first two columns of table 4), and a further example of a fat composition of infant formula in accordance with the invention (third column of table 4); This fat composition of the invention is prepared by e.g. admixing blend 5 of table 2 with an sn-2 palmitic acid enriched fat blend as described in PCT/IL2008/001311.

Table 5 provides the fatty acid profile of compositions (blends) of the invention (Table 2) mixed with an sn-2 palmitic acid enriched fat blend as described in PCT/IL2008/001311.

Table 6 provides milk based infant formula in accordance with the invention; and Table 7 provides soy-based infant formulas in accordance with the present invention.

These infant formula compositions have been formulated in accordance with:

1. Koletzko B. et al. Global Standard for the Composition of Infant Formula: Recommendations of an ESPGHAN Coordinated International Expert Group. *Journal of Pediatric Gastroenterology and Nutrition* 41(5):584-599 (2005).
2. Alles M. et al. Current trends in the composition of infant milk formulas. *Current Paediatrics* 14 (1): 51-63 (2004).
3. Mathews A. Comparison of Triglycerides and Phospholipids as Supplemental Sources of Dietary Long-Chain Polyunsaturated Fatty Acids in Piglets. *J. Nutr.* 132: 3081-3089 (2002).

An infant formula is thus prepared, comprising proteins, carbohydrates, fat, minerals, vitamins, etc. to yield a food product supplying an infant with the major nutrients also found in human milk. 1 liter of reverse osmosis (RO) water is added to a high shear mixer and heated to 70° C. Mixer is turned on at high speed and 480 gr of lactose are added gradually. Mixer speed is reduced and 250 gr of a fat blend (e.g. a fat blend essentially as described in PCT/IL2008/001311) is added. Thereafter 140 gr of skimmed milk, 90 gr of whey protein concentrate and 20 gr of a mixture of minerals, vitamins and trace elements are added. To the obtained mixture, 20 gr of an LC-PUFA enriched lipid composition of the invention, (Table 2) is added. The resulting mixture is passed through a pressure homogenizer and then spray dried to obtain around 1 Kg of dried powder. Since the fat blend of the infant formula is further mixed with an LC-PUFA enriched blend composition of the invention, the fatty acids composition in the infant formula results from the combination of the fatty acids composition of both the fat blend and of the LC-PUFA enriched blend composition of the invention.

TABLE 3

| Fat composition in infant formula: | | | |
|---|---|---|---|
| Fatty acid (% of total fat) | Conventional formula | Formula supplemented with TG as sources of AA and DHA | Formula in accordance with the invention supplemented with TG and PL as sources of AA and DHA |
| C12:0 | 8 ± 0.8 | 8 ± 0.8 | 8 ± 0.8 |
| C14:0 | 3 ± 0.3 | 3 ± 0.3 | 3 ± 0.3 |
| C16:0 | 21 ± 4 | 21 ± 4 | 21 ± 4 |
| C18:0 | 3 ± 0.3 | 3 ± 0.3 | 3 ± 0.3 |
| C18:1n-9 | 46 ± 6 | 44 ± 6 | 44 ± 6 |
| C18:2n-6 | 16 ± 1.6 | 15 ± 1.5 | 15 ± 1.5 |
| C18:3n-3 | 1.5 ± 0.15 | 1.2 ± 0.12 | 1.2 ± 0.12 |
| C20:4n-6 | | 0.6 | 0.6 |
| C22:6n-3 | | 0.3 | 0.3 |
| Phospholipids (g/100 g) | | | |
| Total | ND | ND | 1.35 |
| PC | ND | ND | 0.95 |
| PE | ND | ND | 0.25 |
| PI | ND | ND | 0.05 |
| PA | ND | ND | 0.1 |
| PS | ND | ND | >0.1 |

TG = triglyceride
PL = phospholipids
ND = not detected

TABLE 4

Fat composition in infant formula:

| Fatty acid % w/w | Conventional formula | Formula supplemented with TG as sources of AA and DHA | Formula in accordance with the invention supplemented with TG and PL as sources of AA and DHA |
|---|---|---|---|
| C12 | 8.7 | 8.7 | 8.4 |
| C14 | 3.5 | 3.5 | 3.4 |
| C16 | 21.0 | 21.0 | 20.7 |
| C18 | 2.7 | 2.7 | 2.7 |
| C18:1n9 | 44.4 | 44.4 | 42.9 |
| C18:2 n6 | 16.4 | 16.4 | 15.9 |
| C18:3 n3 | 1.5 | 1.5 | 1.6 |
| C20:3n6 | | | 0.1 |
| C20:4n6 | | 0.7 | 0.7 |
| C20:5n3 | | | 0.1 |
| C22:5n3 | | | 0.2 |
| C22:6n3 | | 0.5 | 0.5 |
| % phospholipids | ND | ND | 1.5 |

ND = not detected

Table 5 describes fat fractions comprising fat blends from table 2. Fats 1-6 of Table 5 are derived from blends 1, 2, 4, 5, 8 and 9 of Table 2 and further comprise at least one triglyceride of formula I which has the following conjugated fatty acid profile:

- 0-10% C8:0 fatty acids out of the total fatty acids;
- 0-10% C10:0 fatty acids out of the total fatty acids;
- 0-22% C12:0 fatty acids out of the total fatty acids;
- 0-15% C14:0 fatty acids out of the total fatty acids;
- 15-55% C16:0 fatty acids out of the total fatty acids of which at least 30% is conjugated at the sn-2 position of triglyceride;
- 1-7% C18:0 fatty acids out of the total fatty acids;
- 20-75% C18:1 fatty acids out of the total fatty acids;
- 2-40% C18:2 fatty acids out of the total fatty acids;
- 0-8% C18:3 fatty acids out of the total fatty acids; and
- other fatty acids present in levels of less than 8% of the total fatty acids.

TABLE 5

| | fat 1 | fat 2 | fat 3 | fat 4 | fat 5 | fat 6 |
|---|---|---|---|---|---|---|
| sn-2 palmitic acid enriched fat blend (%) | 95 | 93.4 | 96.5 | 96 | 97 | 95 |
| blend 1 (%) | 5.0 | | | | | |
| blend 2 (%) | | 6.6 | | | | |
| blend 4 (%) | | | 3.5 | | | |
| blend 5 (%) | | | | 4.0 | | |
| blend 8 (%) | | | | | 3.0 | |
| blend 9 (%) | | | | | | 5 |
| % Phospholipids | 2.6 | 1.4 | 0.6 | 1.5 | 1.5 | 3.1 |
| % Triglycerides | 97.1 | NC | NC | NC | 98.3 | 96.7 |
| Fatty acid % w/w of total fatty acids | | | | | | |
| C12 | 8.3 | 8.1 | 8.4 | 8.4 | 8.4 | 8.3 |
| C14 | 3.4 | 3.4 | 3.4 | 3.4 | 3.4 | 3.4 |
| C16 | 20.7 | 20.5 | 20.8 | 20.7 | 20.7 | 20.7 |
| C18 | 2.8 | 2.8 | 2.8 | 2.7 | 2.8 | 2.8 |
| C18:1n9 | 42.5 | 41.9 | 43.2 | 42.9 | 43.4 | 42.4 |
| C18:2 n6 | 15.7 | 15.6 | 16 | 15.9 | 16.1 | 15.7 |
| C18:3 n3 | 1.5 | 1.6 | 1.6 | 1.6 | 1.6 | 1.5 |
| C20:3n6 | 0.1 | 0.1 | 0.1 | 0.1 | 0.1 | 0.1 |
| C20:4n6 | 1.1 | 1.4 | 1.1 | 0.7 | 0.9 | 0.9 |
| C20:5n3 | 0.1 | 0.1 | <0.1 | 0.1 | <0.1 | 0.1 |
| C22:5n3 | 0.3 | 0.3 | 0.1 | 0.2 | <0.1 | 0.4 |
| C22:6n3 | 0.7 | 0.7 | 0.2 | 0.5 | 0.1 | 0.8 |
| LC-PUFA | | | | | | |
| Total LC-PUFA % w/w | 19.5 | 19.7 | 19.1 | 19.1 | 18.8 | 19.5 |
| % LC-PUFA esterified to PL from total LC-PUFA | 5.6 | 2.8 | 1.1 | 2 | 2.9 | 6.8 |
| AA:DHA | 1.6 | 2.1 | 5.5 | 1.4 | 16.2 | 1.6 |

NC = not calculated

TABLE 6

Milk based infant formula composition:

| | unit | Powder (100 gr) |
|---|---|---|
| General: | | |
| Protein | gram | 11.1 |
| Fat | gram | 25.9 |
| Lactose | gram | 55.5 |
| Water | gram | 2.5 |
| Ash | gram | 2.06 |
| Vitamins: | | |
| Vitamin A | IU | 1500 |
| Vitamin D | IU | 300 |
| Vitamin E | mg | 6 |
| Vitamin K | µg | 15 |
| Vitamin B1 | µg | 350 |
| Vitamin B2 | µg | 450 |
| Vitamin B6 | µg | 222 |
| Vitamin B12 | µg | 0.66 |
| Niacin | mg | 2 |
| Folic acid | µg | 45 |
| Calcium | mg | 4.44 |
| Pantothenate | mg | 3 |
| Biotin | µg | 11 |
| Vitamin C | mg | 45 |
| Minerals | | |
| Calcium | mg | 326 |
| Phosphorus | mg | 219 |
| Magnesium | mg | 37 |
| Iron | mg | 7.4 |
| Sodium | mg | 120.7 |
| Potassium | mg | 373 |
| Ca/P ratio | | 1.49 |
| Amino acid profile | | |
| Alanine | mg | 522 |
| Arginine | mg | 368 |
| Asparatic acid | mg | 11.1 |
| Cysteine | mg | 191 |
| Glutamic acid | mg | 1423 |
| Glycine | mg | 244 |
| Histidine | mg | 262 |
| Isoleucine | mg | 761 |
| Leucine | mg | 12.2 |
| Lysine | mg | 10 |
| Methionine | mg | 270 |
| Phenylalanine | mg | 461 |
| Proline | mg | 962 |
| Serine | mg | 681 |
| Taurine | mg | 37 |
| Threonine | mg | 686 |
| Tryptophan | mg | 180 |
| Tyrosine | mg | 463 |
| Valine | mg | 775 |

TABLE 7

Soy based infant formula:

| | unit | Powder (100 gr) |
|---|---|---|
| General: | | |
| Protein | gr | 15 |
| Fat | gr | 27.54 |

TABLE 7-continued

| Soy based infant formula: | | |
|---|---|---|
| | unit | Powder (100 gr) |
| Carbohydrate | gr | 51.5 |
| Linoleic acid | gr | 4.5 |
| | Vitamins: | |
| Vitamin A | IU | 1500 |
| Vitamin D | IU | 300 |
| Vitamin E | IU | 10 |
| Vitamin C | mg | 65 |
| Vitamin K | μg | 77 |
| Vitamin B1 | μg | 345 |
| Vitamin B2 | μg | 445 |
| Vitamin B6 | μg | 327 |
| Vitamin B12 | μg | 1.5 |
| Niacin | mg | 7 |
| Folic acid | μg | 76 |
| Pantothenic acid | μg | 4.5 |
| Biotin | μg | 25 |
| Choline | mg | 58 |
| | Minerals | |
| Calcium | mg | 500 |
| Phosphorus | mg | 300 |
| Magnesium | mg | 45 |
| Iron | mg | 9.2 |
| Zinc | mg | 4 |
| Manganese | μg | 150 |
| Copper | μg | 400 |
| Iodine | μg | 77 |
| Sodium | mg | 200 |
| Potassium | mg | 546 |
| Chloride | mg | 400 |
| Inositol | mg | 25 |
| Carnitine | mg | 10 |
| Ca/P ratio | | 1.67 |
| | Amino acid profile | |
| Alanine | mg | 640 |
| Arginine | mg | 497 |
| Asparatic acid | mg | 1385 |
| Cysteine | mg | 242 |
| Glutamic acid | mg | 3065 |
| Glycine | mg | 300 |
| Histidine | mg | 382 |
| Isoleucine | mg | 893 |
| Leucine | mg | 1600 |
| Lysine | mg | 1360 |
| Methionine | mg | 406 |
| Phenylalanine | mg | 650 |
| Proline | mg | 1113 |
| Serine | mg | 737 |
| Taurine | mg | 51 |
| Threonine | mg | 460 |
| Tyrosine | mg | 621 |
| Valine | mg | 947 |

Infant formulas designed to mimic the different lactation periods can be prepared by controlling the levels of fat blend and of LC-PUFA enriched blend composition of the invention.

Example 3

Effect of DHA and AA Conjugated Phospholipids in Infant Formula on Cognitive Development and Visual Acuity The study includes three groups of infants fed with three infant formulas that differ only in their LC-PUFA fat content (Table 3).

Group I receives standard infant formula without DHA and AA supplementation.

Group II receives infant formula supplemented with standard DHA and AA supplementation (i.e., DHA and AA conjugated to triglycerides only).

Group III receives infant formula supplemented in accordance with the present invention, particularly with DHA and AA conjugated to triglycerides and phospholipids (i.e., a mix of DHA and AA conjugated to triglycerides and to phospholipids, whereas the ratio of the conjugated triglycerides and phospholipids is 1:1).

The cognitive development of the infants is measured by the Bayley scales test (essentially as described in Pinelli J et al. *Adv Neonatal Care* 3(2):76-87 (2003)). The visual acuity of the infants is measured by the visual evoked acuity test (essentially as described in Innis S M. *J Pediatr.* 139(4):532-8 (2001)). Both tests are adapted to the age of the infants. During the 6 months of formula feeding, the tests are performed at baseline and during the study approximately every one to two months. The infants in the third group (fed with infant formula comprising the DHA and AA conjugated to triglycerides and phospholipids according to the invention) demonstrate better cognitive development and visual acuity as compared to the infants in the other two groups.

Example 4

Effect of DHA and AA Conjugated to Phospholipids Within Diet on Cognitive Function Development in an Animal Model The fatty acid (FA) docosahexaenoic acid (DHA, 22: 6n-3) is highly enriched in membrane phospholipids of the central nervous system and retina. Neuronal pathways, such as those involved in learning, memory, spatial learning, etc. indicate cognitive function development. In this study, a systematic assessment of neurodevelopmental and cognitive milestones is performed in animal pups. The analyses include measurements of physical growth and maturation and evaluation of neurological reflexes.

Study Design

Animals are fed with different diets and appearance of neural reflexes and reflex performance is examined after birth.

Study design is carried out according to Kiss et al, Development of Neurological Reflexes and Motor Coordination in Rats Neonatally Treated with Monosodium Glutamate, *Neurotoxicity Research,* 2005, VOL. 8(3,4). pp. 235-244.

Diets

The animals received diets essentially as described in Table 3 or Table 4:

Group I: reference diet, normal chow.

Group II: a synthetic diet whose fat source is enriched with DHA and AA esterified to triglycerides (TG) only.

Group III: synthetic diet: fat source is enriched with DHA and AA esterified to triglycerides (TG) and phospholipids (PL) (for example, fat blends 1-9, Table 2).

Growth

Weight is recorded every day until 3 weeks of age, then weekly. Body length (nasoanal length) is measured weekly.

Neurological Signs and Reflexes

Examinations of neurobehavioral development are started on the first postnatal day and carried out daily until postnatal day 21. Inspections are carried out for maturation of physical characteristics such as eye opening, incisor eruption and ear unfolding. Pups are tested for the following neurological signs and reflexes:

1. Righting reflex: rats are placed in a supine position and the time in seconds to turn over to a prone position and place all four paws in contact with the surface is recorded.

2. Negative geotaxis: animals are placed head down on an inclined board (45° C.) of 30 cm. The hindlimbs of the pups are placed in the middle of the board. The day they begin to turn around and climb up the board with their forelimbs reaching the upper rim is observed. From the day of the appearance of the negative geotaxis, the time in seconds to reach the upper end of the board is recorded daily.

3. Sensory reflexes: the ear and the eyelid are gently touched with a cotton swab and the first day of the ear twitch reflex and the contraction of the eyelid are recorded.

4. Limb placing: the back of the forepaw and hindpaw is touched with the edge of the bench with the animal suspended, and the first day of lifting and placing the paws on the table is noted.

5. Limb grasp: the fore- and hind-limbs are touched with a thin rod, and the first day of grasping onto the rod is recorded.

6. Gait: the animals are placed in the center of a white paper circle of 13 cm in diameter, and the day they begin to move off the circle with both forelimbs is recorded. From the day of the appearance, the time in seconds to move off the circle is recorded daily.

7. Auditory startle: the first day of the startle response to a clapping sound is observed.

In conclusion, the results show that feeding animals with diet enriched with a composition of the invention enhances the development of neural system.

Example 5

Effect of DHA and AA Conjugated to Phospholipids Within Diet on Retina of an Animal Model The fatty acid (FA) docosahexaenoic acid (DHA, 22: 6n-3) is highly enriched in membrane phospholipids of the central nervous system and retina. G protein-coupled receptor (GPCR) signal transduction is a common signaling motif in neuronal pathways, such as those involved in learning, memory, olfactory-based discrimination, spatial learning, and visual acuity.

Study design is according to Niu et al, 2004, Reduced G Protein-coupled Signaling Efficiency in Retinal Rod Outer Segments in Response to n-3 Fatty Acid Deficiency, J. Biol. Chem., Vol. 279, Issue 30, 31098-31104.

Study Design

Animals are obtained at weaning (3 weeks of age). Weaning females are randomly divided into dietary groups with the constraint that both groups had the same mean body weight; the animals are divided to groups so that the mean weight of the animals in both group is similar. The females in both dietary groups are mated, the offspring are culled, and the dams are maintained on their respective diets during lactation. At the age of 21 days, the pups are dark-adapted overnight and sacrificed by decapitation under dim red light.

Diets

The animals received diets essentially as described in Table 3 or Table 4:

Group I: reference diet, normal chow.

Group II: a synthetic diet whose fat source is enriched with DHA and AA esterified to triglycerides (TG) only.

Group III: synthetic diet whose fat source is enriched with DHA and AA esterified to triglycerides (TG) and phospholipids (PL) (for example, see table 2, fat blends 1-9).

Retina

G protein-coupled receptor (GPCR) signaling in retinal rod outer segment (ROS) membranes isolated from rats fed with the different diets is studied. GPCR signaling is assessed in different steps: rhodopsin activation, rhodopsin-transducin coupling, cGMP phosphodiesterase activity, and formation of metarhodopsin II (MII) and the MII-$G_t$ complex.

Further, fatty acid composition in retina is measured.

Feeding animals with diet enriched with a composition of the invention results in higher signaling in retinal rod outer segment and in higher LC-PUFA content in retina.

Example 6

Effect of DHA and AA Conjugated to Phospholipids Within Diet on Retina and Visual Acuity in an Animal Model Electroretinography measures electrical responses of various cell types in the retina, including the photoreceptors (rods and cones), inner retinal cells (bipolar and amacrine cells), and the ganglion cells. During a recording, the eyes are exposed to standardized stimuli and the resulting signal is displayed showing the time course of the signal's amplitude (voltage).

Study design is according to Kraft et al, 1987, The Rat Electroretinogram in Combined Zinc and Vitamin A Deficiency, Investigative Opthalmology & Visual Science.

Study Design

To assess the retinal function, animals are raised in dim illumination with different diets and Scotopic electroretinograms (ERGs) is performed.

Diets

The animals received diets essentially as described in Table 3 or Table 4:

Group I: reference diet, normal chow.

Group II: a synthetic diet whose fat source is enriched with DHA and AA esterified to triglycerides (TG) only.

Group III: synthetic diet whose fat source is enriched with DHA and AA esterified to triglycerides (TG) and phospholipids (PL) (for example, see table 2, fat blends 1-9).

Electroretinography

Scotopic ERGs are measured on animals at regular intervals during the course of the experiment. Prior to the ERGs, animals are dark-adapted for a minimum period of 12 hr. A standard EEG (Electroencephalogram) needle electrode is placed into the anterior chamber of the eye and a reference electrode is placed subcutaneously into the skin of the head near the upper eyelid to record the ERG. The eye is subjected to single stimulus flashes of increasing intensity. The ERG is displayed on an oscilloscope and recorded on magnetic tape.

Animals in group III, that receive diet enriched with a composition of the invention demonstrate higher retinal sensitivity.

Example 7

Effect of DHA and AA Conjugated Phospholipids Within Diet on Growth and Brain and CNS Development in an Animal Model The mammalian brain is particularly rich in long-chain polyunsaturated fatty acids (PUFA), especially docosahexaenoic acid (DHA) [22:6(n-3)] and arachidonic acid (AA) [20:4(n-6)]. Maternal dietary DHA and AA effect on the composition of rat pup myelin is examined in an animal model. Dietary lipids play an important role in myelin synthesis, particularly during the period of maximum myelination. The studies are conducted during the period of maximum myelination, which coincides with the onset of hearing in rat pups.

Study design is according to Haubner et al, 2007, The Effects of Maternal Dietary Docosahexaenoic Acid Intake on Rat Pup Myelin and the Auditory Startle Response, Dev Neurosci 29:460-467.

Study Design:

Timed-pregnant dams are received on day 2 of gestation. Upon arrival, dams are assigned to be fed with different diets, with free access to diets and water. Fresh diet is provided to the dams throughout pregnancy and lactation. The day of birth is designated as postnatal day (PND) 0. Dams from each diet group and their randomized litters are assigned to the study. Pups are weaned on PND 21 and then fed the corresponding maternal diets until PND 24 when they are killed by decapitation. Cerebrum and cerebellum are removed from pups per diet group for fatty acids analysis.

Diets

The animals received diets essentially as described in Table 3 or Table 4:

Group I: reference diet, normal rat chow

Group II: a synthetic diet whose fat source is enriched with DHA and AA esterified to triglycerides (TG) only.

Group III: synthetic diet whose fat source is enriched with DHA and AA esterified to triglycerides (TG) and phospholipids (PL) (for example, see table 2, fat blends 1-9).

Biochemical Analyses

The fatty acid composition of total lipid extracts prepared from diets is determined by gas liquid chromatography. Homogenates of brain tissue obtained from all pups on PND 24 are prepared and myelin is isolated. The fatty acid composition of myelin is measured in total lipid extract prepared from the brains.

Group III, that receive diet enriched with a composition of the invention demonstrate higher levels of DHA and AA in pup myelin.

Example 8

Effect of DHA and AA Conjugated Phospholipids Within Diet on Fatty Acid Composition in the Blood and the Brain of an Animal Model Given that members of the (n-3) and (n-6) families compete for the same desaturase enzymes, the effects of the supplementation of PUFA from one family on tissue deposition of the PUFA from the other family may be an important factor to consider when determining which dietary PUFA composition is optimal for neural development. Therefore, using the artificial rearing model to directly feed infant rats experimental formulae during the period of rapid brain development, allows for the precise control of both the relative and absolute amounts of specific dietary PUFA. Furthermore, this method allows for the direct delivery of the diet to the pups during a period of brain development that roughly parallels the third trimester and early postnatal period in humans or early infancy in the preterm infant.

Study design is according to Ward et al, 1998, Long-Chain Polyunsaturated Fatty Acid Levels in Formulae Influence Deposition of Docosahexaenoic Acid and Arachidonic Acid in Brain and Red Blood Cells of Artificially Reared Neonatal Rats, The Journal of Nutrition Vol. 128 No. 12 December, pp. 2473-2487.

Study Design

The pregnant dams are obtained at 10-12 days gestation and housed individually with free access to diet and tap water. Offspring of timed-pregnant animals are culled, when necessary, within 24 h of birth, and approximately equal numbers of male and female offspring are selected as subjects. Pups are assigned randomly to groups diets. Milk substitutes with or without DHA and/or AA, are fed from days 5-18 of life, which are the period of rapid brain development.

Diets

The animals received diets essentially as described in Table 3 or Table 4:

Group I: reference diet, normal rat chow.

Group II: a synthetic diet whose fat source is enriched with DHA and AA esterified to triglycerides (TG) only.

Group III: synthetic diet whose fat source is enriched with DHA and AA esterified to triglycerides (TG) and phospholipids (PL) (for example, see table 2, fat blends 1-9).

Artificial Rearing Procedure

On Day 27 post conception (approximately Day 5 after birth), pups are anesthetized, and the gastrostomy tube is inserted into the mouth, down the esophagus, and out through the stomach wall. Pups are housed individually fed one of the experimental diets via tubing. Each day, all pups are weighed to assess growth. Suckled control pups are not gastrostomized, but are fostered to nursing dams on the day of gastrostomy. On day 40 postconception (approximately day 18 postbirth), animals are sacrificed, blood is removed by cardiac puncture, and brains are removed and divided into FB and CB.

Biochemical Analysis.

Fatty acid composition is assessed in both the blood and the brain to study the relationship between brain and Red Blood Cells (RBC) composition. The brain is subdivided into forebrain (FB) and cerebellum (CB) because, in rats, developmental events that occur prenatally in the FB occur to a large extent postnatally in the CB. Therefore, dietary effects that have specific effects on rapidly developing tissue should, during the early postnatal period in rats, produce greater effects on the CB than on the FB.

Group III, that receive diet enriched with a composition of the invention demonstrate higher levels of DHA and AA in blood and brain, meaning better intestinal absorption.

The invention claimed is:

1. A composition, comprising:

at least one triglyceride comprising a compound of formula I:

$$R_1O-\underset{H_2}{C}-\underset{|}{\overset{OR_2}{CH}}-\underset{H_2}{C}-OR_3 \quad (I)$$

wherein $R_1$, $R_2$ and $R_3$ may be identical or different and are each independently selected from the group consisting of H or an acyl group, wherein the acyl group is selected from the group consisting of a saturated fatty acid, a mono-unsaturated fatty acid and long chain poly-unsaturated fatty acid (LC-PUFA) residues; and at least one long chain poly-unsaturated fatty acid (LC-PUFA); and at least one phospholipid comprising a compound of formula II:

(II)

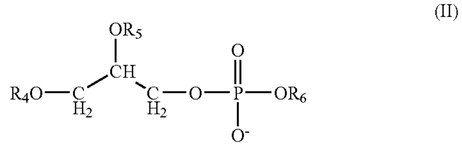

wherein $R_4$ and $R_5$ are each a substituent having independently the meanings of $R_1$, $R_2$, $R_3$, and in which $R_6$ is selected from the group consisting of choline, inositol, ethanolamine and serine;

wherein the total amount of phospholipids is at least 15%;

and further wherein at least 1% of the LC-PUFA in the composition is conjugated to the at least one phospholipid.

2. The composition of claim 1, wherein at least 2% of the LC-PUFA content of the composition is conjugated to the at least one phospholipid.

3. The composition of claim 2, wherein at least 5% of the LC-PUFA content of the composition is conjugated to the at least one phospholipid.

4. The composition of claim 3, wherein at least 10% of the LC-PUFA content of the composition is conjugated to the at least one phospholipid.

5. The composition of claim 4, wherein at least 20% of the LC-PUFA content of the composition is conjugated to the at least one phospholipid.

6. The composition of claim 5, wherein at least 50% of the LC-PUFA content of the composition is conjugated to the at least one phospholipid.

7. The composition of claim 1, wherein the LC-PUFA is selected from the group consisting of an omega-3 fatty acid, an omega-6 fatty acid, and combinations of any thereof.

8. The composition of claim 1, wherein the LC-PUFA comprises a component selected from the group consisting of docosahexaenoic acid (DHA), arachidonic acid (AA), and combinations of any thereof.

9. The composition of claim 8, wherein the weight content of AA is larger than that of DHA.

10. The composition of claim 9, wherein the weight content ratio between AA and DHA is at least 1.1.

11. The composition of claim 10, wherein the weight content ratio between AA and DHA is at least 1.3.

12. The composition of claim 11, wherein the weight content ratio between AA and DHA is at least 1.5.

13. The composition of claim 12, wherein the weight content ratio between AA and DHA is at least 2.

14. The composition of claim 13, wherein the weight content ratio between AA and DHA is at least 3.

15. The composition of claim 14, wherein the weight content ratio between AA and DHA is at least 10.

16. The composition of claim 1, wherein $R_5$ comprises an LC-PUFA residue.

17. The composition of claim 16, wherein the LC-PUFA residue comprises an omega-3 or an omega-6 fatty acid residue.

18. The composition of claim 17, wherein the LC-PUFA comprises docosahexaenoic acid (DHA) or arachidonic acid (AA).

19. The composition of anyone of claim 16, wherein $R_4$ is an LC-PUFA residue.

20. The composition of claim 1, wherein the total amount of phospholipids is at least 20%.

21. The composition of claim 20, wherein the total amount of phospholipids is at least 35%.

22. The composition of claim 21, wherein the total amount of phospholipids is at least 50%.

23. The composition of claim 1, wherein the triglyceride and the phospholipid are derived from at least one raw lecithin material selected from the group consisting of vegetable, marine, aquaculture organisms, and combinations of any thereof.

24. The composition of claim 1 further comprising at least one triglyceride of formula I, having at least 30% (w/w) of total palmitic acid conjugated at the sn-2 position.

25. The composition of claim 1 further comprising at least one triglyceride of formula I having the following conjugated fatty acid profile:

0-10% C8:0 fatty acids out of the total fatty acids;

0-10% C10:0 fatty acids out of the total fatty acids;

0-22% C12:0 fatty acids out of the total fatty acids;

0-15% C14:0 fatty acids out of the total fatty acids;

15-55% C16:0 fatty acids out of the total fatty acids of which at least 30% is conjugated at the sn-2 position of triglyceride;

1-7% C18:0 fatty acids out of the total fatty acids;

20-75% C18:1 fatty acids out of the total fatty acids;

2-40% C18:2 fatty acids out of the total fatty acids;

0-8% C18:3 fatty acids out of the total fatty acids; and other fatty acids present in levels of less than 8% of the total fatty acids.

26. A composition selected from the group consisting of a pharmaceutical, a nutraceutical, a functional food, and an infant formula, the composition comprising the composition of claim 1.

27. A method of treatment of a condition in an infant comprising administering to the infant the composition of claim 1, wherein the treatment of the condition is selected from the group consisting of improving, promoting or maintaining the development of cognitive functions in an infant, improving, promoting or maintaining the development of brain and retina in an infant, improving, promoting or maintaining the development of visual acuities in an infant, reducing lipid peroxidation in an infant, improving, promoting or maintaining the growth quality of an infant, improving, promoting or maintaining the CNS development in an infant, enhancing intestinal absorption of omega-3 and/or omega-6 fatty acids in healthy, non-healthy and preterm infants, improving, promoting or maintaining intestinal maturity in infants, and combinations of any thereof.

28. A method of preparation of a pharmaceutical or neutraceutical composition for treatment of infants comprising including the composition of claim 1 in the pharmaceutical or neutraceutical composition.

29. The method of claim 28, wherein the treatment comprises treatment of an infant for a condition selected from the group consisting of improving, promoting or maintaining the development of cognitive functions in an infant, improving, promoting or maintaining the development of brain and retina in an infant, improving, promoting or maintaining the development of visual acuities in an infant, reducing lipid peroxidation in an infant, improving, promoting or maintaining the growth quality of an infant, improving, promoting or maintaining the CNS development in an infant, enhancing intestinal absorption of omega-3 and/or omega-6 fatty acids in healthy, non-healthy and preterm infants, improving, promoting or maintaining intestinal maturity in infants, and combinations of any thereof.

30. The composition of claim 8 wherein the LC-PUFA is DHA.

* * * * *